United States Patent
Sakami et al.

(10) Patent No.: US 9,024,074 B2
(45) Date of Patent: May 5, 2015

(54) METHOD FOR PRODUCING P-XYLENE AND/OR P-TOLUALDEHYDE

(71) Applicant: Toray Industries, Inc., Tokyo (JP)

(72) Inventors: Satoshi Sakami, Kamakura (JP); Daijiro Tsukamoto, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 14/374,449

(22) PCT Filed: Jan. 23, 2013

(86) PCT No.: PCT/JP2013/051323

§ 371 (c)(1),
(2) Date: Jul. 24, 2014

(87) PCT Pub. No.: WO2013/111782

PCT Pub. Date: Aug. 1, 2013

(65) Prior Publication Data

US 2014/0378710 A1    Dec. 25, 2014

(30) Foreign Application Priority Data

Jan. 26, 2012 (JP) ................................ 2012-013944

(51) Int. Cl.
| | |
|---|---|
| *C07C 45/66* | (2006.01) |
| *C07C 45/69* | (2006.01) |
| *C07C 1/22* | (2006.01) |
| *B01J 23/26* | (2006.01) |
| *C07C 1/207* | (2006.01) |
| *B01J 23/42* | (2006.01) |
| *B01J 23/44* | (2006.01) |
| *B01J 23/46* | (2006.01) |
| *B01J 23/72* | (2006.01) |
| *B01J 23/745* | (2006.01) |
| *B01J 23/755* | (2006.01) |
| *C07C 45/65* | (2006.01) |
| *C07C 45/61* | (2006.01) |

(52) U.S. Cl.
CPC ............. *C07C 45/69* (2013.01); *B01J 23/26* (2013.01); *C07C 1/207* (2013.01); *C07C 2101/16* (2013.01); *B01J 23/42* (2013.01); *B01J 23/44* (2013.01); *B01J 23/462* (2013.01); *B01J 23/72* (2013.01); *B01J 23/745* (2013.01); *B01J 23/755* (2013.01); *C07C 45/65* (2013.01); *C07C 1/22* (2013.01); *C07C 45/61* (2013.01); *C07C 2523/42* (2013.01); *C07C 2523/44* (2013.01); *C07C 2523/46* (2013.01); *C07C 2523/755* (2013.01)

(58) Field of Classification Search
CPC ............ C07C 45/61; C07C 45/69; C07C 1/22
USPC .................................................. 568/433, 321
See application file for complete search history.

(56) References Cited

FOREIGN PATENT DOCUMENTS

| | | |
|---|---|---|
| JP | 51-86437 A | 7/1976 |
| WO | WO 2011/044243 A1 | 4/2011 |

OTHER PUBLICATIONS

International Search Report dated Apr. 16, 2013, application No. PCT/JP2013/051323.
Kugatova, G.P.; Poskiene, R. Aromatization of 2-methyl- and 4-methyl-▲3- tetrahydrobenzaldehydes, Lietuvos TSR Mokslu Akad. Darbai Ser. B, 1960, No. 2, p. 157-61.
Tetrahedron Letters, 2011, vol. 52, p. 7157-60.
Chemical Abstracts, vol. 49, 1955, 45408-4541b, (Zhurnal Obshchei Khimii (1954), 24, 298-302).
Organic Letters, 2006, vol. 8, No. 12, p. 2487-2489.
Yoichi Suzuki, Kiyoshi Mashimo and Tatsuaki Yamaguchi, "Organic Resource Chemistry", Sankyo Publishing Co., Ltd., published on Oct. 10, 2008, pp. 204-205.
Chemical Engineering Journal, vol. 154, issue 1-3, pp. 396-400 (2009).
Chemistry A European Journal, vol. 17, issue 44, pp. 12452-12457 (2011).

*Primary Examiner* — Sikarl Witherspoon
(74) *Attorney, Agent, or Firm* — RatnerPrestia

(57) ABSTRACT

Disclosed is a method for producing p-xylene and/or p-tolualdehyde with high yield through a short process using biomass resource-derived substances as raw materials. The method for producing p-xylene and/or p-tolualdehyde of the present invention comprises: a cyclization step of producing 4-methyl-3-cyclohexenecarboxaldehyde from isoprene and acrolein; and an aromatization step of producing p-xylene and/or p-tolualdehyde from 4-methyl-3-cyclohexenecarboxaldehyde by gas-phase flow reaction using a catalyst(s).

22 Claims, 1 Drawing Sheet

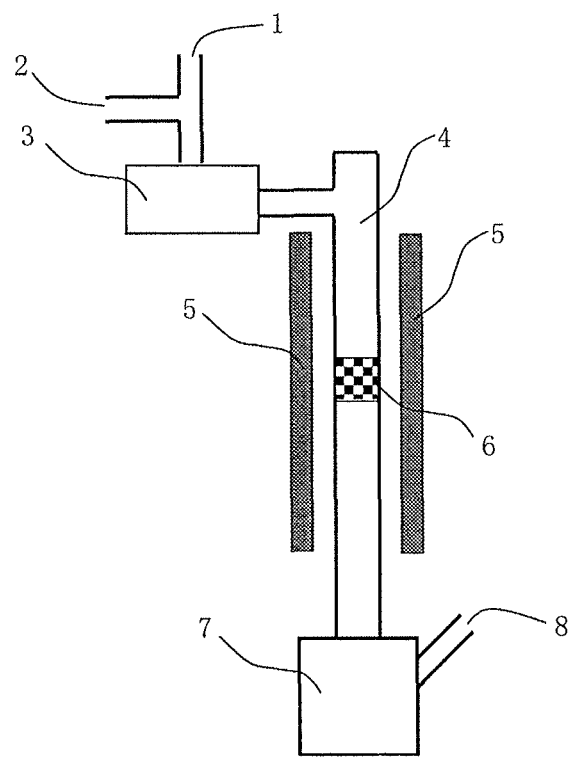

METHOD FOR PRODUCING P-XYLENE AND/OR P-TOLUALDEHYDE

CROSS REFERENCE TO RELATED APPLICATIONS

This is the U.S. National Phase application of PCT/JP2013/051323, filed Jan. 23, 2013, which claims priority to Japanese Patent Application No. 2012-013944, filed Jan. 26, 2012, the disclosures of each of these applications being incorporated herein by reference in their entireties for all purposes.

FIELD OF THE INVENTION

The present invention relates to a method for producing p-xylene and/or p-tolualdehyde using as a raw material a biomass resource-derived substance that can be derived from biomass resources.

BACKGROUND OF THE INVENTION p-Xylene is a raw material for terephthalic acid, which is an intermediate material for polyester, and the like, and important as a basic chemical product in the chemical industry. p-Xylene is industrially produced using as a raw material a fossil resource such as petroleum or natural gas. Industrial production of terephthalic acid from p-xylene is carried out by, for example, air oxidation in an acetic acid solvent by using acetic acid salts of cobalt and manganese as catalysts and sodium bromide as a promoter (Non-patent Document 1).

Similarly to p-xylene, p-tolualdehyde is a useful chemical product that can be converted into terephthalic acid. Production of terephthalic acid from p-tolualdehyde can be carried out by, for example, a method similar to the above-mentioned air oxidation that uses p-xylene as a raw material (Patent Document 1).

Recently, on the other hand, depletion of oil resources, and global warming due to greenhouse gases such as carbon dioxide generated from fossil resources are becoming serious. Therefore, in order to achieve switching to a sustainable, recycling-oriented society, techniques for producing chemical products from substances derived from biomass resources, which are renewable resources, need to be constructed urgently.

In the chemical industry, switching of raw materials from fossil resources to biomass resources is being intensively studied. Among such studies, in order to replace raw materials for terephthalic acid, and eventually raw materials for polyester, with a biomass resource-derived substance(s), methods for producing p-xylene from a biomass resource-derived substance are being studied. For example, Non-patent Document 2 discloses a method for producing a hydrocarbon including p-xylene by a chemical conversion step using as a raw material ethanol, which can be produced from a biomass resource, and a zeolite catalyst. Patent Document 2 discloses a method for producing p-xylene by the chemical conversion steps of dehydration, dimerization and cyclization-dehydrogenation, using as a raw material isobutanol obtained from a biomass resource. Non-patent Document 3 discloses a method for producing p-xylene by the chemical conversion steps of cyclization, oxidization, dehydration and decarboxylation, using as raw materials 2,5-dimethylfuran and acrolein derived from biomass resource-derived substances.

PATENT DOCUMENTS

Patent Document 1: JP S51-86437 A
Patent Document 2: WO 2011/044243

NON-PATENT DOCUMENTS

Non-patent Document 1: Yoichi Suzuki, Kiyoshi Mashimo and Tatsuaki Yamaguchi, "Organic Resource Chemistry", Sankyo Publishing Co., Ltd., published on Oct. 10, 2008, pp. 204-205.

Non-patent Document 2: Chemical Engineering Journal, vol. 154, issue 1-3, pp. 396-400 (2009).

Non-patent Document 3: Chemistry A European Journal, vol. 17, issue 44, pp. 12452-12457 (2011).

SUMMARY OF THE INVENTION

As described above, several techniques for producing p-xylene as a raw material for terephthalic acid using a substance derived from a biomass resource have been disclosed. However, in any of these methods, the yield of p-xylene is low, and a large number of steps are required, which are problematic.

In the production method disclosed in Non-patent Document 2, the weight yield of the mixture of p-xylene and meta-xylene is up to 6.21%, which corresponds to 10.8% in terms of the molar yield. Thus, the yield of p-xylene is extremely low.

In the production method disclosed in Patent Document 2, a large-scale equipment and heavy economic burden are required since the chemical conversion process proceeds in as long as 3 steps. Further, in the step of chemical conversion from isobutanol in this method, the weight yield of p-xylene is 18.7%, which corresponds to 26.1% in terms of the molar yield. Thus, the yield is low.

The production method disclosed in Non-patent Document 3 has many problems. For example, the chemical conversion process proceeds in as long as 4 steps; the oxidation step requires a large amount of harmful hydrogen peroxide, and also requires a solvent; and the decarboxylation step requires an expensive solvent.

Thus, development of a method for producing p-xylene and/or p-tolualdehyde, which is/are used as a raw material(s) for terephthalic acid, using a biomass resource-derived substance(s) as a raw material(s) with high yield through a short process has been strongly demanded. The present invention aims to provide a method for producing p-xylene and/or p-tolualdehyde using biomass resource-derived substances as raw materials, with higher yield and by a shorter process than in conventional methods.

As a result of intensive study to solve the above problems, the present inventors discovered a method for producing p-xylene and/or p-tolualdehyde with high yield through a short process using biomass resource-derived substances isoprene and acrolein as raw materials, thereby completing the present invention.

That is, the present invention includes a method for producing p-xylene and/or p-tolualdehyde from isoprene and acrolein, which method comprises: a cyclization step of producing 4-methyl-3-cyclohexenecarboxaldehyde from isoprene and acrolein; and an aromatization step of producing p-xylene and/or p-tolualdehyde from 4-methyl-3-cyclohexenecarboxaldehyde by gas-phase flow reaction using a catalyst(s).

The production method of an embodiment of the present invention can be described by the reaction equation below.

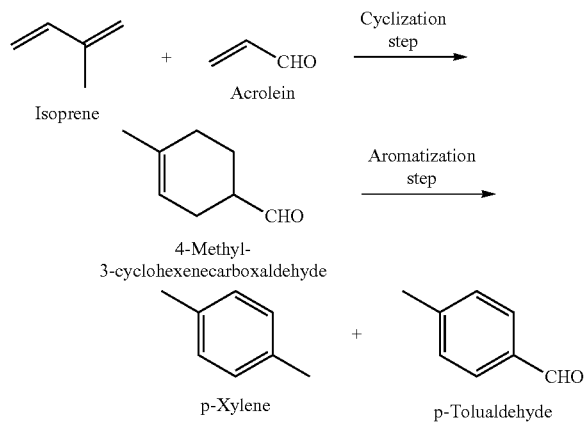

In an embodiment of the present invention, the catalyst used in the aromatization step is a catalyst comprising a carrier carrying a metal(s) and/or metal oxide(s), and examples of the embodiment include an embodiment using a catalyst comprising a carrier carrying at least one metal and/or metal oxide selected from the group consisting of platinum, nickel, palladium, ruthenium, platinum oxide, copper oxide, iron oxide and chromium oxide, an embodiment using a carrier selected from the group consisting of alumina, silica-alumina, silica, zeolite, titania, magnesia and carbon, and an embodiment using chromium oxide-carrying alumina, chromium oxide-carrying silica-alumina or chromium oxide-carrying silica.

In an embodiment of the present invention, the reaction temperature in the gas-phase flow reaction in the aromatization step is 300° C. to 500° C.

In an embodiment of the present invention, the cyclization step is a step that is carried out in the presence of a catalyst comprising a Lewis acid.

By the present invention, p-xylene and/or p-tolualdehyde can be produced using biomass resource-derived substances as raw materials, with higher yield and by a shorter process than in conventional methods.

BRIEF DESCRIPTION OF THE DRAWING

FIG. 1 is a diagram illustrating an example of a gas-phase flow reactor of the fixed-bed flow type.

DETAILED DESCRIPTION OF EMBODIMENTS OF THE INVENTION

In the present invention, the biomass resource means a regenerative organic resource derived from organisms, and means a resource composed of an organic matter(s) produced by carbon dioxide fixation using solar energy by plants. Specific examples of the biomass resource include maize, sugarcane, tubers, wheat, rice, soybean, pulp, kenaf, rice straw, wheat straw, bagasse, corn stover, switchgrass, weeds, waste paper, woods, charcoal, natural rubber, cotton, soybean oil, palm oil, safflower oil and castor oil.

In the present invention, the substance derived from a biomass resource (biomass resource-derived substance) means a substance that is derived, can be derived, or was derived from the above-described biomass resource by fermentation, chemical conversion or the like. The present invention includes the feature that isoprene and acrolein, which can be obtained as biomass resource-derived substances, can be used as raw materials, but does not exclude use of isoprene and acrolein derived from a fossil resource(s) such as petroleum, as raw materials.

Isoprene as a raw material of the present invention can be obtained from a biomass resource. For example, as disclosed in Industrial Biotechnology, vol. 6, issue 3, pp. 152-163 (2010), biomass resource-derived isoprene can be produced by fermentation of glucose obtained by saccharification of maize or the like.

As for another raw material in the present invention, acrolein, one derived from a fossil resource is commercially available and hence can be easily obtained.

The biomass resource-derived acrolein can be produced by dehydration of glycerol derived from a biomass resource (Green Chemistry, vol. 9, issue 10, pp. 1130-1136 (2007)). The biomass resource-derived glycerol can be produced by, for example, solvolysis of an oil such as soybean oil or palm oil, or fermentation from glucose.

The biomass resource-derived acrolein can also be produced by oxidation of biomass resource-derived propylene. The biomass resource-derived propylene can be produced by, for example, chemical conversion using as a raw material a plant-derived fatty alcohol such as bioethanol, bioisopropanol or biobutanol.

The present invention includes a method for producing p-xylene and/or p-tolualdehyde, which method is characterized in that the method comprises:

a cyclization step of producing 4-methyl-3-cyclohexenecarboxaldehyde from isoprene and acrolein; and an aromatization step of producing p-xylene and/or p-tolualdehyde from 4-methyl-3-cyclohexenecarboxaldehyde by gas-phase flow reaction using a catalyst(s), The cyclization reaction in the present invention may produce, in addition to 4-methyl-3-cyclohexenecarboxaldehyde, its positional isomer 3-methyl-3-cyclohexenecarboxaldehyde. In this cyclization reaction, acid catalysts effectively act on the progress of the reaction and selective production of 4-methyl-3-cyclohexenecarboxaldehyde. Preferred examples of the acid catalyst include catalysts containing a Lewis acid such as aluminum chloride, titanium tetrachloride, zinc chloride, zinc bromide, boron fluoride and scandium triflate; and catalysts containing a Brønsted acid such as a boronic acid derivative. More preferred examples of the acid catalyst include acid catalysts containing aluminum chloride or zinc chloride. Aluminum chloride, aluminum chloride-tetrahydrofuran complex and zinc chloride-choline chloride complex are especially preferred.

The cyclization step in the present invention can be carried out in the presence of a solvent or in the absence of a solvent. Examples of the solvent that are preferably used include paraffin hydrocarbons such as pentane, hexane and cyclohexane; aromatic hydrocarbons such as benzene, toluene and xylene; alkyl halides such as dichloromethane, chloroform, carbon tetrachloride and 1,2-dichloroethane; and ethers such as diethyl ether, tetrahydrofuran and 1,4-dioxane.

In the cyclization step in the present invention, in cases where no acid catalyst is used, the reaction temperature is preferably 100° C. to 200° C. In cases where an acid catalyst(s) is/are used, the reaction temperature is preferably −70° C. to 50° C., more preferably −20° C. to 30° C.

In the cyclization step in the present invention, preferred examples of the combination of reaction conditions that may be applied include conditions where the reaction is carried out in the absence of a solvent, using aluminum chloride or an aluminum chloride-tetrahydrofuran complex as the acid catalyst at a reaction temperature within the range of, for example, 0° C. to 30° C. (disclosed in Organic Letters, vol. 8, issue 12, pp. 2487-2489 (2006)), and conditions where the reaction is carried out in the absence of a solvent, using a zinc chloride-choline chloride complex as the acid catalyst at a reaction temperature within the range of, for example, 0° C. to 30° C. (disclosed in Green Chemistry, vol. 4, pp. 24-26 (2002)).

The step of aromatization of 4-methyl-3-cyclohexenecarboxaldehyde in the present invention is optionally carried out by gas-phase flow reaction using a catalyst(s). The catalyst used in this reaction may be the later-mentioned hydrogenation catalyst used in the hydrogenation reaction or the later-mentioned dehydrogenation catalyst used in the dehydrogenation reaction.

An aromatization reaction of 4-methyl-3-cyclohexenecarboxylic acid, which has a structure similar to 4-methyl-3-cyclohexenecarboxaldehyde, is disclosed in Journal of Organic Chemistry, vol. 40, issue 9, pp. 1287-1292 (1975). In this disclosure, a liquid-phase batch reaction is carried out in the presence of a palladium/active carbon catalyst, but this condition is not suitable for aromatization of 4-methyl-3-cyclohexenecarboxaldehyde because of a low yield (see Comparative Example 1). On the other hand, in the gas-phase flow reaction using a hydrogenation catalyst or dehydrogenation catalyst of the present invention, aromatization proceeds efficiently, and p-xylene and/or p-tolualdehyde can be produced with excellent yield from 4-methyl-3-cyclohexenecarboxaldehyde.

As the hydrogenation catalyst in the aromatization step, a catalyst normally used for hydrogenation of an aromatic compound, olefin, carbonyl group or the like may be employed. Specific examples of the hydrogenation catalyst that may be preferably used include simple metals such as nickel, cobalt, copper, chromium, gold, palladium, ruthenium and rhodium, and oxides of these metals; and catalysts containing any of these simple metals and these metal oxides (e.g., catalysts in which any of these simple metals and these metal oxides is supported by a carrier).

Examples of the dehydrogenation catalyst that may be used in the aromatization step include catalysts used for dehydrogenation of aliphatic hydrocarbons, alcohols and the like. Specific examples of the dehydrogenation catalyst that may be preferably used include metals or metal oxides such as copper, chromium oxide, copper oxide, iron oxide, palladium and platinum; and catalysts containing any of these metals or metal oxides (e.g., catalysts in which any of these simple metals or metal oxides is supported by a carrier).

The carrier that carries the catalyst used in the aromatization step is a substance that retains a substance having a catalytic activity (e.g., the simple metals and metal oxides described above) in a dispersed state on its surface, and specific examples of the carrier include alumina, silica-alumina, silica, zeolite, titania, magnesia, zirconia, diatomaceous earth and carbon.

The catalyst used in the aromatization step in the present invention is preferably a catalyst in which the metal(s) and/or metal oxide(s) described above is/are supported by the carrier described above. More specifically, the catalyst is more preferably a catalyst comprising the above-described carrier that carries at least one metal or metal oxide selected from the group consisting of platinum, nickel, palladium, ruthenium, platinum oxide, copper oxide, iron oxide and chromium oxide.

Preferred examples of the combination of the metal or metal oxide and the carrier in the catalyst used in the aromatization step in the present invention include platinum on alumina, platinum on silica-alumina, platinum on silica, platinum on carbon, nickel on carbon, nickel on alumina, nickel on silica-alumina, nickel on silica, palladium on alumina, palladium on carbon, palladium on silica-alumina, palladium on silica, ruthenium on alumina, ruthenium on silica-alumina, ruthenium on silica, ruthenium on carbon, chromium oxide on alumina, chromium oxide on silica-alumina and chromium oxide on silica. Chromium oxide on alumina, chromium oxide on silica-alumina and chromium oxide on silica are especially preferred.

The reaction mode of the gas-phase flow reaction in the aromatization step is a reaction performed by placing a solid catalyst in a tubular reactor and allowing a vaporized reaction material (in an embodiment of the present invention, 4-methyl-3-cyclohexenecarboxaldehyde) to pass through the catalyst layer. Examples of the type of the gas-phase flow reaction include the fixed-bed flow type, in which a catalyst is left to stand; the moving-bed flow type, in which a catalyst is moved; and the fluidized-bed flow type, in which a catalyst is allowed to flow. Any of these reaction types may be applied to the gas-phase flow reaction in the present invention.

Examples of the reaction apparatus of the fixed-bed flow type include the apparatus exemplified in FIG. 1. The apparatus of FIG. 1 is constituted by a reaction tube 4; a vaporizer 3 having a raw material inlet 1 and a carrier gas inlet 2; a crude reaction liquid capture container (condenser) 7; and a tubular furnace 5. A catalyst layer 6 can be fixed inside the reaction tube 4. The reaction tube 4 can be heated to a desired temperature by the tubular furnace 5. The gas-phase flow reaction using the apparatus of FIG. 1 can be carried out by supplying a raw material from the raw material inlet 1 to the vaporizer 3, and then introducing the vaporized raw material to the reaction tube 4. The raw material may also be introduced together with a carrier gas to the reaction tube 4. The product can be captured as a liquid in the crude reaction liquid capture container 7, or as a gas from a gas outlet 8.

In the gas-phase flow reaction in the aromatization step, the pressure inside the reactor is not limited, and preferably 0.001 MPa to 0.5 MPa. The reaction can be simply carried out under atmospheric pressure without using an apparatus or operation for reducing or increasing the pressure.

In the gas-phase flow reaction in the aromatization step, a carrier gas may be allowed to flow together with the raw reaction material into the reactor. Preferred examples of the carrier gas include inert gases such as argon, helium and nitrogen. These inert gases may contain water vapor, air, oxygen, hydrogen and/or the like. The mixing ratio between the raw reaction material and the carrier gas may be appropriately selected.

In the gas-phase flow reaction in the aromatization step, the contact time, which is a physical quantity given by W/F (h) wherein the supply rate of the raw reaction material (in an embodiment of the present invention, 4-methyl-3-cyclohexenecarboxaldehyde) is represented as F (g/h) and the catalyst weight is represented as W (g), is preferably 0.01 h to 10 h, more preferably 0.05 h to 2 h.

The reaction temperature during the gas-phase flow reaction in the aromatization step is preferably 300° C. to 500° C.

EXAMPLES

Embodiments of the present invention are described below in more detail by way of Examples. However, the present invention is not limited to the Examples below.

The conversion, selectivity and yield represented in the Examples and Comparative Examples below were calculated according to the equations (Equation 1), (Equation 2) and (Equation 3) below.

Conversion (%)=((Amount of raw material before reaction−Amount of raw material after reaction)/Amount of raw material before reaction)×100  (Equation 1)

Selectivity (%)=(Amount of product)/(Amount of raw material before reaction−Amount of raw material after reaction)×100  (Equation 2)

Yield (%)=(Amount of product/Amount of raw material before reaction)×100  (Equation 3)

In Examples 2-8, the reaction apparatus of the fixed-bed flow type shown in FIG. 1 was used in the gas-phase flow reaction. The apparatus had a quartz reaction tube 4 having an inner diameter of 6 mm and a total length of 300 mm; a vaporizer 3 having a carrier gas inlet 2 and a raw material inlet 1, which vaporizer 3 was located on the top of the reaction tube; and a crude reaction liquid capture container (condenser) 7 having a gas outlet 8, which container 7 was located at the lower end of the reaction tube. A catalyst was placed in the reaction tube such that the catalyst was fixed at the center of the tube, and the catalyst layer 6 was heated with a ceramic electric tubular furnace 5 (Asahi Rika Seisakusyo Co., Ltd., ARF-20KC, furnace inner length: 200 mm). During the reaction, the reaction liquid capture container 7 was cooled in an ice bath, and the crude reaction liquid was captured. In Examples 2-4, the organic layer was separated from the captured crude reaction liquid, and the weight of the layer was measured. A known amount of ethanol as an internal standard was added to the organic layer, and the resulting mixture was subjected to $^1$H-NMR analysis. From the ratio between the integrated values of the peak of each compound and the peak of ethanol in the organic layer, the content of each compound was calculated to determine the conversion, selectivity and yield. In Examples 5-8, the total weight of the captured crude reaction liquid was measured, and the crude reaction liquid was diluted with acetonitrile to prepare 20 mL of a dilution, which was then subjected to gas chromatography analysis. From a calibration curve prepared using standard samples for each compound and the peak area value of each compound, the content of each compound was calculated to determine the conversion, selectivity and yield.

Example 1

Production of 4-Methyl-3-Cyclohexenecarboxaldehyde (Cyclization Step)

After replacing the atmosphere in a 25-mL evaporating flask with argon, a stirrer and aluminum chloride (530 mg) were placed therein, and the content was cooled to 0° C. and stirred. Tetrahydrofuran (0.64 mL) was added to the flask, and the resulting mixture was stirred at the same temperature for 15 minutes, followed by adding acrolein (13.4 mL) and isoprene (20 mL) thereto, and then stirring the mixture at 25° C. for 72 hours. After adding 1 mol/L aqueous sodium hydroxide solution (12 mL) to the mixture, extraction with chloroform was performed. The organic layer was filtered through Celite, and the obtained solution was concentrated with an evaporator to obtain a crude product of 4-methyl-3-cyclohexenecarboxaldehyde. This crude product was subjected to $^1$H-NMR analysis together with a known weight of ethanol (internal standard substance) to calculate the yield of 4-methyl-3-cyclohexenecarboxaldehyde (yield, 68%). The crude product was purified by distillation under reduced pressure to isolate 4-methyl-3-cyclohexenecarboxaldehyde (yield, 65%).

Reference Example 1

Preparation of Chromium Oxide on Alumina (Catalyst A)

Chromium (III) nitrate nonahydrate (7.7 g) was dissolved in distilled water (25 mL), and alumina (JGC Catalysts and Chemicals Ltd., N613N) (19 g) was added to the resulting solution. The obtained suspension was stirred on a hot plate heated at 120° C. to evaporate water. The resulting solid was placed on an evaporating dish, and calcination was carried out at 500° C. for 4 hours to obtain Catalyst A.

Reference Example 2

Preparation of Chromium Oxide on Silica-alumina (Catalyst B)

Catalyst B was prepared by the same method as in Reference Example 1 except that silica-alumina (JGC Catalysts and Chemicals Ltd., N633HN; 66.5% silica, 25.1% alumina) (19 g) was used instead of alumina.

Reference Example 3

Preparation of Chromium Oxide on Silica (Catalyst C)

Catalyst C was prepared by the same method as in Reference Example 1 except that silica (Fuji Silysia Chemical Ltd., CARiACT G3) (19 g) was used instead of alumina.

Example 2

Aromatization Step by Gas-Phase Flow Reaction Using Catalyst A

Catalyst A (200 mg) was placed in the reaction tube, and the tubular furnace was heated at 400° C. Nitrogen was allowed to flow from the top of the reaction tube at a flow rate of 10 mL/min. Two hours later, while the tubular furnace was kept at 400° C. and while nitrogen as a carrier gas was allowed to flow from the top of the reaction tube at a flow rate of 10 ml/min, 4-methyl-3-cyclohexenecarboxaldehyde obtained in Example 1 was supplied to the catalyst layer at 1.88 g/h together with the nitrogen flow. Thirty minutes later, 767 mg of an organic layer was obtained from the capturing container at the lower end of the reaction tube. The content of each compound in the organic layer was calculated to determine the conversion, selectivity and yield. The results are shown in Table 1.

Example 3

Aromatization Step by Gas-Phase Flow Reaction Using Catalyst B (1)

The reaction was performed by the same method as in Example 2 except that Catalyst B (200 mg) was used instead of Catalyst A (200 mg), and the conversion, selectivity and yield were calculated. The results are shown in Table 1.

Example 4

Aromatization Step by Gas-Phase Flow Reaction Using Catalyst B (2)

The reaction was performed by the same method as in Example 3 except that the temperature of the tubular furnace was set to 300° C. instead of 400° C., and the conversion, selectivity and yield were calculated. The results are shown in Table 1.

Example 5

Aromatization Step by Gas-Phase Flow Reaction Using Catalyst C

The reaction was performed by the same method as in Example 2 except that Catalyst C (200 mg) was used instead of Catalyst A (200 mg), to obtain 795 mg of a crude reaction liquid. The content of each compound in the crude reaction liquid was calculated to determine the conversion, selectivity and yield. The results are shown in Table 1.

Example 6

Aromatization Step by Gas-Phase Flow Reaction Using Platinum on Alumina (Catalyst D)

The reaction was performed by the same method as in Example 5 except that Catalyst D (N.E. Chemcat Corporation, containing 5% platinum, 200 mg) was used instead of Catalyst C (200 mg), and the conversion, selectivity and yield were calculated. The results are shown in Table 1.

Example 7

Aromatization Step by Gas-Phase Flow Reaction Using Palladium on Alumina (Catalyst E)

The reaction was performed by the same method as in Example 5 except that Catalyst E (N.E. Chemcat Corporation, containing 5% palladium, 200 mg) was used instead of Catalyst C (200 mg), and the conversion, selectivity and yield were calculated. The results are shown in Table 1.

Example 8

Aromatization Step by Gas-Phase Flow Reaction Using Ruthenium on Alumina (Catalyst F)

The reaction was performed by the same method as in Example 5 except that Catalyst F (N.E. Chemcat Corporation, containing 5% ruthenium and 53.17% water, 200 mg) was used instead of Catalyst C (200 mg), and the conversion, selectivity and yield were calculated. The results are shown in Table 1.

Comparative Example 1

Aromatization Step by Batch Reaction

Under argon atmosphere, a stirrer, palladium on active carbon (Catalyst G) (N.E. Chemcat Corporation, containing 10% palladium, 100 mg), and 4-methyl-3-cyclohexenecarboxaldehyde obtained in Example 1 (500 mg) were placed in a 20-mL reaction container, and the mixture was heated at 200° C. with stirring. One and a half hours later, the reaction liquid was cooled to room temperature, and ethanol (70.1 mg) as an internal standard was added to the reaction liquid, followed by stirring the resulting mixture. The obtained mixed liquid was subjected to $^1$H-NMR analysis, and, from the ratio between the integrated values of the peak of each compound and the peak of ethanol in the mixed liquid, the amount of the compound produced was calculated to determine the conversion, selectivity and yield. The results are shown in Table 1.

TABLE 1

| | | Catalyst | | Selectivity (%) | | Yield (%) | |
| --- | --- | --- | --- | --- | --- | --- | --- |
| | Reaction mode | Reaction temperature | Conversion (%) | p-Xylene | p-Tolualdehyde | p-Xylene | p-Tolualdehyde |
| Example 2 | Gas-phase flow reaction | Catalyst A 400° C. | 93 | 44 | 5 | 41 | 4 |
| Example 3 | Gas-phase flow reaction | Catalyst B 400° C. | 100 | 34 | 0 | 34 | 0 |
| Example 4 | Gas-phase flow reaction | Catalyst B 300° C. | 54 | 38 | 0 | 20 | 0 |
| Example 5 | Gas-phase flow reaction | Catalyst C 400° C. | 94 | 42 | 5 | 40 | 5 |
| Example 6 | Gas-phase flow reaction | Catalyst D 400° C. | 91 | 28 | 4 | 25 | 4 |
| Example 7 | Gas-phase flow reaction | Catalyst E 400° C. | 62 | 24 | 6 | 15 | 4 |
| Example 8 | Gas-phase flow reaction | Catalyst F 400° C. | 47 | 17 | 8 | 8 | 4 |
| Comparative Example 1 | Batch reaction | Catalyst G 200° C. | 93 | 3 | 2 | 3 | 2 |

From Examples 2-8, it was shown that p-xylene and/or p-tolualdehyde can be produced from 4-methyl-3-cyclohexenecarboxaldehyde with excellent yield by the gas-phase flow reaction.

Further, from Examples 2-8 and Comparative Example 1, it was shown that the gas-phase flow reaction produces p-xylene and/or p-tolualdehyde with higher yield than the batch reaction.

Furthermore, from Examples 2-8 and Comparative Example 1, it was shown that the gas-phase flow reaction results in a very high selectivity of p-xylene and/or p-tolualdehyde, and that the batch reaction results in a low selectivity. Thus, it was shown that, in cases where an unreacted raw material is present (that is, in cases where the conversion is less than 100%), the gas-phase flow reaction can increase the yield by recovery and reuse of the raw material, while the batch reaction can hardly increases the yield even by recovery and reuse of the raw material.

Furthermore, from Examples 1-8, it was shown that p-xylene and/or p-tolualdehyde can be produced with high yield through a short process from isoprene and acrolein.

By the present invention, p-xylene and/or p-tolualdehyde can be produced with high yield through a short process from isoprene and acrolein, which can be derived from biomass resources. Further, since, by the present invention, the raw materials for chemical products such as terephthalic acid and polyester that are produced from p-xylene or p-tolualdehyde can be switched from fossil resources to biomass resources, the present invention can contribute to switching to a sustainable, recycling-oriented society. Thus, the present invention is industrially very useful.

DESCRIPTION OF SYMBOLS

1 Raw material inlet
2 Carrier gas inlet
3 Vaporizer
4 Reaction tube
5 Tubular furnace
6 Catalyst layer
7 Crude reaction liquid capture container (condenser)
8 Gas outlet

The invention claimed is:

1. A method for producing p-xylene and/or p-tolualdehyde, said method comprising:
   a cyclization step of producing 4-methyl-3-cyclohexenecarboxaldehyde from isoprene and acrolein; and
   an aromatization step of producing p-xylene and/or p-tolualdehyde from 4-methyl-3-cyclohexenecarboxaldehyde by gas-phase flow reaction using a catalyst(s).

2. The production method according to claim 1, wherein the catalyst used in the aromatization step comprises a carrier which carries a metal(s) and/or metal oxide(s).

3. The production method according to claim 1, wherein the catalyst used in the aromatization step comprises a carrier which carries at least one metal or metal oxide, said metal or metal oxide being selected from the group consisting of platinum, nickel, palladium, ruthenium, platinum oxide, copper oxide, iron oxide and chromium oxide.

4. The production method according to claim 1, wherein the catalyst used in the aromatization step comprises a carrier selected from the group consisting of alumina, silica-alumina, silica, zeolite, titania, magnesia and carbon.

5. The production method according to claim 1, wherein the catalyst used in the aromatization step is chromium oxide on alumina, chromium oxide on silica-alumina or chromium oxide on silica.

6. The production method according to claims 1, wherein the reaction temperature in the gas-phase flow reaction in the aromatization step is 300° C. to 500° C.

7. The production method according to claim 1, wherein the cyclization step is carried out in the presence of a catalyst comprising a Lewis acid.

8. The production method according to claim 2, wherein the catalyst used in the aromatization step comprises a carrier which carries at least one metal or metal oxide, said metal or metal oxide being selected from the group consisting of platinum, nickel, palladium, ruthenium, platinum oxide, copper oxide, iron oxide and chromium oxide.

9. The production method according to claim 2, wherein the catalyst used in the aromatization step comprises a carrier selected from the group consisting of alumina, silica-alumina, silica, zeolite, titania, magnesia and carbon.

10. The production method according to claim 3, wherein the catalyst used in the aromatization step comprises a carrier selected from the group consisting of alumina, silica-alumina, silica, zeolite, titania, magnesia and carbon.

11. The production method according to claim 2, wherein the catalyst used in the aromatization step is chromium oxide on alumina, chromium oxide on silica-alumina or chromium oxide on silica.

12. The production method according to claim 3, wherein the catalyst used in the aromatization step is chromium oxide on alumina, chromium oxide on silica-alumina or chromium oxide on silica.

13. The production method according to claim 4, wherein the catalyst used in the aromatization step is chromium oxide on alumina, chromium oxide on silica-alumina or chromium oxide on silica.

14. The production method according to claim 2, wherein the reaction temperature in the gas-phase flow reaction in the aromatization step is 300° C. to 500° C.

15. The production method according to claim 3, wherein the reaction temperature in the gas-phase flow reaction in the aromatization step is 300° C. to 500° C.

16. The production method according to claim 4, wherein the reaction temperature in the gas-phase flow reaction in the aromatization step is 300° C. to 500° C.

17. The production method according to claim 5, wherein the reaction temperature in the gas-phase flow reaction in the aromatization step is 300° C. to 500° C.

18. The production method according to claim 2, wherein the cyclization step is carried out in the presence of a catalyst comprising a Lewis acid.

19. The production method according to claim 3, wherein the cyclization step is carried out in the presence of a catalyst comprising a Lewis acid.

20. The production method according to claim 4, wherein the cyclization step is carried out in the presence of a catalyst comprising a Lewis acid.

21. The production method according to claim 5, wherein the cyclization step is carried out in the presence of a catalyst comprising a Lewis acid.

22. The production method according to claim 6, wherein the cyclization step is carried out in the presence of a catalyst comprising a Lewis acid.

* * * * *